(12) United States Patent
Govari

(10) Patent No.: US 10,777,318 B2
(45) Date of Patent: Sep. 15, 2020

(54) PHYSICIAN RELATED SELECTIVE DATA COMPRESSION

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 115 days.

(21) Appl. No.: 16/102,223

(22) Filed: Aug. 13, 2018

(65) Prior Publication Data
US 2020/0051683 A1  Feb. 13, 2020

(51) Int. Cl.
| | |
|---|---|
| G06K 9/00 | (2006.01) |
| G16H 30/40 | (2018.01) |
| G16H 10/60 | (2018.01) |
| A61B 5/04 | (2006.01) |
| A61B 5/0402 | (2006.01) |

(52) U.S. Cl.
CPC .......... *G16H 30/40* (2018.01); *A61B 5/0402* (2013.01); *A61B 5/04012* (2013.01); *G16H 10/60* (2018.01)

(58) Field of Classification Search
USPC ....................................................... 382/128
See application file for complete search history.

(56) References Cited

U.S. PATENT DOCUMENTS

| | | | | |
|---|---|---|---|---|
| 6,016,442 A | * | 1/2000 | Hsu .................... | A61N 1/37247 600/518 |
| 7,697,983 B1 | | 4/2010 | Oza | |
| 9,215,075 B1 | | 12/2015 | Poltorak | |
| 9,477,701 B1 | | 10/2016 | Kundu | |
| 2004/0006265 A1 | | 1/2004 | Alhussiny | |
| 2004/0249672 A1 | * | 12/2004 | Bocionek ............... | G16H 10/60 705/2 |
| 2007/0140536 A1 | * | 6/2007 | Sehnert ................. | G06F 19/321 382/128 |
| 2007/0288556 A1 | * | 12/2007 | Anton ................ | H04N 21/2312 709/203 |
| 2010/0119146 A1 | * | 5/2010 | Inazumi .................. | G06T 5/003 382/153 |
| 2010/0217139 A1 | * | 8/2010 | Pinter .................... | A61B 5/024 600/508 |
| 2012/0257698 A1 | | 10/2012 | Zhang | |
| 2013/0231947 A1 | | 9/2013 | Shusterman | |

(Continued)

OTHER PUBLICATIONS

European Search Report for corresponding EPA No. 19191243.5 dated Jan. 15, 2020.

*Primary Examiner* — Stephen P Coleman

(57) ABSTRACT

An apparatus includes a network interface and a processor. The network interface is configured to communicate over a communication network. The processor is configured to receive (i) data, including a medical parameter acquired as a function of time, and (ii) a selection of one or more time intervals of interest within the time period. The processor is further configured to compress a first portion of the data, which is within the selected time intervals, at a first resolution, and compress a second portion of the data, which is outside the selected time intervals, at a second resolution, which is coarser than the first resolution. The processor is additionally configured to transmit the compressed first and second portions of the data, via the network interface, over the communication network.

20 Claims, 3 Drawing Sheets

(56) References Cited

U.S. PATENT DOCUMENTS

| | | | |
|---|---|---|---|
| 2014/0112578 A1* | 4/2014 | Wang | A61B 8/0866 |
| | | | 382/165 |
| 2014/0194762 A1 | 7/2014 | Kuppuraj et al. | |
| 2017/0300654 A1 | 10/2017 | Stein et al. | |
| 2017/0332931 A1 | 11/2017 | Szymkiewicz et al. | |

* cited by examiner

PHYSICIAN RELATED SELECTIVE DATA COMPRESSION

FIELD OF THE INVENTION

The present invention relates generally to processing and remotely displaying patient health data, and particularly to electrophysiological data compression for uploading to a remote server.

BACKGROUND OF THE INVENTION

Various known methods were proposed to facilitate remote diagnosis of medical conditions, such as heart problems. For example, U.S. Patent Application Publication 2014/0194762 describes a method for displaying patient electrocardiogram (ECG) data. The method includes receiving ECG data including an ECG waveform; receiving analyzed ECG data including arrhythmic events; generating an indication of the detected arrhythmic event; and displaying the indication of the detected arrhythmic event in relation to the ECG waveform at a position associated with a time of the detected arrhythmic event. A system for displaying patient ECG data is also disclosed.

As another example, U.S. Patent Application Publication 2013/0231947 describes an adaptive system for medical monitoring that distributes data processing among computing devices connected to a network, to optimize usage of computational resources, network communication speed and user experience. Data processing is distributed into several levels with bi-directional communication between the levels (computing devices) to coordinate and adjust data compression, filtering, and analysis, as well as the size of buffered data available for transmission and/or receiving.

U.S. Patent Application Publication 2017/0300654 describes telemedicine systems and methods. A controller of the system can establish, using the transceiver, a telemedicine session with the operations center using a Transport Morphing Protocol (TMP), the TMP being an acknowledgement-based user datagram protocol. The controller can also mask one or more transient network degradations to increase resiliency of the telemedicine session. The telemedicine system can include a 2D and 3D carotid Doppler and transcranial Doppler and/or other diagnostic devices, and provides for real-time connectivity and communication between medical personnel in an emergency vehicle and a receiving hospital for immediate diagnosis and treatment to a patient in need.

SUMMARY OF THE INVENTION

An embodiment of the present invention provides an apparatus including a network interface and a processor. The network interface is configured to communicate over a communication network. The processor is configured to receive (i) data, including a medical parameter acquired as a function of time, and (ii) a selection of one or more time intervals of interest within the time period. The processor is further configured to compress a first portion of the data, which is within the selected time intervals, at a first resolution, and compress a second portion of the data, which is outside the selected time intervals, at a second resolution, which is coarser than the first resolution. The processor is additionally configured to transmit the compressed first and second portions of the data, via the network interface, over the communication network.

In some embodiments, the apparatus further includes an input device, configured to receive the selection of the one or more time intervals from a physician.

In some embodiments, the processor is further configured to automatically select the one or more time intervals, based on a given criterion.

In an embodiment, the received data includes one or more electrocardiogram (ECG) traces.

In another embodiment, the processor is configured to select the first resolution based on an average heart rate calculated over the selected time-intervals.

In some embodiments, the processor is configured to select the one or more time-intervals based on one or more indications that an arrhythmia was recorded during the time-intervals.

In some embodiments, the first resolution is at least twice the second resolution.

There is additionally provided, in accordance with an embodiment of the present invention, an apparatus including a network interface and a processor. The network interface is configured to communicate over a communication network. The processor is configured to receive over the communication network, via the network interface, data including a medical parameter acquired as a function of time, wherein the data includes (i) a first portion that is within one or more selected time intervals and is compressed at a first resolution, and (ii) a second portion that is outside the selected time intervals and is compressed at a second resolution, coarser than the first resolution. The processor is further configured to decompress the first and second portions of the data, and process the decompressed data.

In some embodiments, the processor is configured to archive the decompressed data.

In some embodiments, the processor is configured to transmit over the communication network, via the network interface, the decompressed first and second portions of the data to a remote processor.

There is further provided, in accordance with an embodiment of the present invention, a method, including, in a processor, receiving (i) data, including a medical parameter acquired as a function of time, and (ii) a selection of one or more time intervals of interest within the time period. A first portion of the data, which is within the selected time intervals, is compressed at a first resolution. A second portion of the data, which is outside the selected time intervals, is compressed at a second resolution, which is coarser than the first resolution. The compressed first and second portions of the data over a communication network are transmitted.

There is also provided, in accordance with an embodiment of the present invention, a method, including, in a processor, receiving over a communication network data including a medical parameter acquired as a function of time, wherein the data includes (i) a first portion that is within one or more selected time intervals and is compressed at a first resolution, and (ii) a second portion that is outside the selected time intervals and is compressed at a second resolution, coarser than the first resolution. The first and second portions of the data are decompressed, and the decompressed data is processed.

The present invention will be more fully understood from the following detailed description of the embodiments thereof, taken together with the drawings in which:

DETAILED DESCRIPTION OF EMBODIMENTS

Overview

Figure 1:
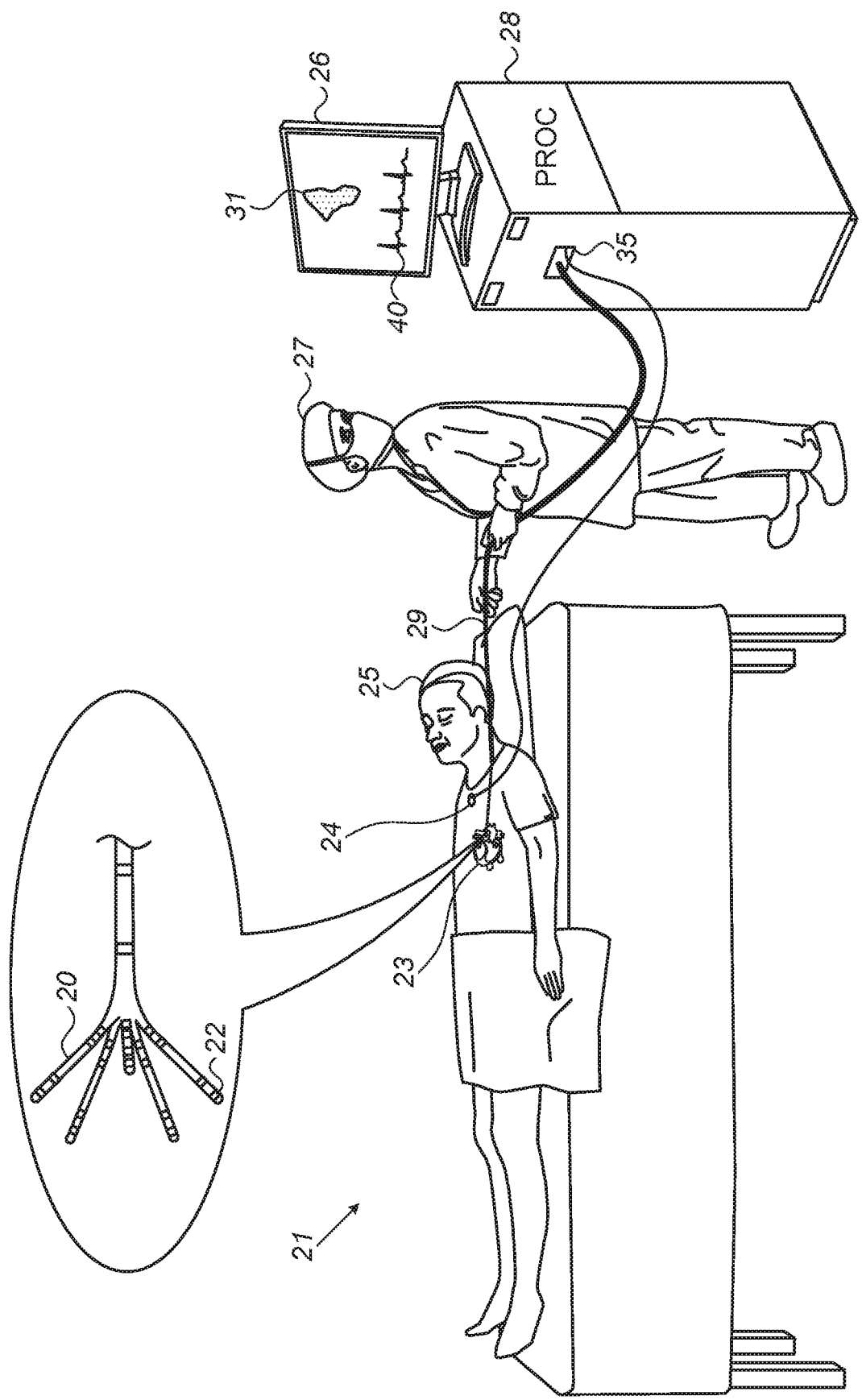
FIG. 1 is a schematic, pictorial illustration of a system for electro-anatomical mapping, in accordance with an embodiment of the present invention.

A medical system that generates electrophysiological (EP) data, such as that characterizing a heart or brain condition, may be required to transmit the data over a communication network to, for example, an internet web-based server, for additional processing, such as storage or analysis. The EP data, e.g., an electrocardiogram (ECG) or an electroencephalogram (EEG), may be subsequently downloaded to a remote computer and displayed for review.

While communicating with the internet web-based server (also named cloud server or remote server), the medical system and the remote computer may encounter difficulties in both directions, to and from the server, for example, due to bandwidth limitations of the network. Typically, though, only a fraction of the acquired displayable data is of clinical significance, so indiscriminately transmitting all of the displayable data may thus be inefficient and may cause delays and/or exceed the available communication bandwidth.

Embodiments of the present invention that are described hereinafter provide a method for compressing medical data, such as the EP data described above, in a "smart" manner. The method enables the use of links having a limited bandwidth to upload large amounts of "smartly" compressed medical data to a cloud server, and to subsequently download the data to a remote processor, which decompresses the data and displays the data on a display located at a remote site.

The smart compression is based on criteria that are set by a physician or automatically by a process of selective compression. In some embodiments, the criteria are specified for selecting time-intervals with data of interest, as described below.

In general, the smart, the selective compression techniques described herein may compress the data by selectively reducing the quantization of the data (e.g., the number of bits used to represent each data value), reducing the sampling rate of the data, or in any other suitable way. The compression may utilize any suitable compression tools. In the present context, any such compression scheme is characterized by a certain resolution. Finer resolution corresponds to better quality in representing the original data, but at the price of higher data volume (and thus transmission bandwidth). Coarser resolution corresponds to smaller data volume, at the expense of some quality degradation.

In some embodiments, a disclosed local client system comprises (i) a network interface, configured to communicate over a communication network, and (ii) a processor, which is configured to receive (a) data, comprising a medical parameter acquired as a function of time, and (b) a selection of one or more time-intervals of interest within the time period. The processor is further configured to compress a first portion of the data, which is within the selected time intervals, at a first resolution, compress a second portion of the data, which is outside the selected time intervals, at a second resolution, which is coarser than the first resolution, and transmit the compressed first and second portions of the data, via the network interface, over the communication network.

In the disclosed description the first resolution is also termed "high resolution," whereas the second resolution is also termed "low resolution." In some embodiments, compressing a portion of data in high resolution means transmitting that portion of data without compressing the data at all.

In some embodiments, the EP data comprises hundreds of ECG channels that were sampled at 32 bit/sec (bps) each. The processor transmits in high resolution time-intervals of a portion of the sampled ECG channels, and transmits the rest of the ECG data in compressed to a lower resolution. The local processor (e.g., client system) transmits in high resolution, for example, only time-intervals of data that were selected by the physician for further analysis and/or review.

The physician may use interactive means (i.e., an input device) to select the first portion of data to be compressed at the first resolution, such as by marking regions using a mouse, a touchscreen and/or a keyboard. In an embodiment, one or more selected sections of displayable data are uploaded over the communication network to a cloud server in high resolution, such as 16-32 bps, while the remaining data is transmitted at a coarser resolution, such as 8 bps.

Alternatively or additionally, an automatic process, such as computer software, may perform a discriminate selection of data for compression, based, for example, on guidelines defined and entered via the input device by the physician. In an embodiment, a set of criteria may be applied, for example, for a software to select time-intervals of data for transmission in high resolution for analysis. An example of such a criterion is a recorded moving average heart rate.

In some embodiments, smart compression is further used in a downlink, in which the "smartly" compressed displayable data is discriminately processed again by, for example, the remote server, which reprocesses the low-resolution data so it will be displayed at even lower resolution, while the high-resolution data is transmitted at a same high resolution.

The disclosed method of selective compression of displayable data by a decision of a physician and/or automatically according to guidelines the physician determines, may improve procedures for remote medical diagnosis. Specifically, the disclosed method would assist in decreasing the amount of data transfer, and by so ease a procedure of remote medical diagnosis.

System Description

FIG. 1 is a schematic, pictorial illustration of a system 21 for electro-anatomical mapping, in accordance with an embodiment of the present invention. FIG. 1 depicts a physician 27 using an electro-anatomical catheter 29 to perform an electro-anatomical mapping of a heart 23 of a patient 25. Catheter 29 comprises, at its distal end, one or more arms 20, to each of which are coupled one or more mapping-electrodes 22. During the mapping procedure, electrodes 22 acquire and/or inject signals from and/or to the tissue of heart 23, such as of intra-cardiac ECG. The respective locations of mapping-electrodes 22 (i.e., where the intra-cardiac ECG signals are measured) are tracked as well, as described below. A processor 28 receives these signals via an electrical interface 35, and processes the information contained in these signals to construct displayable medical data, such as an electro-anatomical map 31 and present ECG traces 40 on a local display 26.

To externally sense electrophysiological data, a plurality of external electrodes 24 are coupled to the body of patient 25; for example, three external electrodes 24 may be coupled to the patient's chest, and another three external electrodes may be coupled to the patient's back. For ease of illustration, only one external electrode is shown in FIG. 1.

An example of a system used for tracking the locations of mapping-electrodes 22 inside heart 23 of the patient is the CARTON system (produced by Biosense Webster, Irvine, Calif.). The CARTON system uses mapping-electrodes 22 to sense potentials induced in heart 23 by applying voltages between external electrodes 24. Based on the sense potentials and given the known positions of electrodes 24 on the patient's body, processor 28 calculates an estimated location of each of electrodes 22 within the patient's heart. The processor may thus associate any given signal received from electrodes 22, such as an electrophysiological signal, with the location at which the signal was acquired.

The example illustration shown in FIG. 1 is chosen purely for the sake of conceptual clarity. Other types of electrophysiological sensing geometries, such as of the Lasso® Catheter (produced by Biosense Webster) may also be employed. Additionally, contact sensors may be fitted at the distal end of electro-anatomical catheter 29 and transmit data indicative of the physical quality of electrode contact with tissue. In an embodiment, measurements of some electrodes 22 may be discarded because their physical contact quality is poor, and the measurements of other electrodes may be regarded as valid because their contact quality is high.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory.

Physician Related Selective Data Compression

Figure 2:
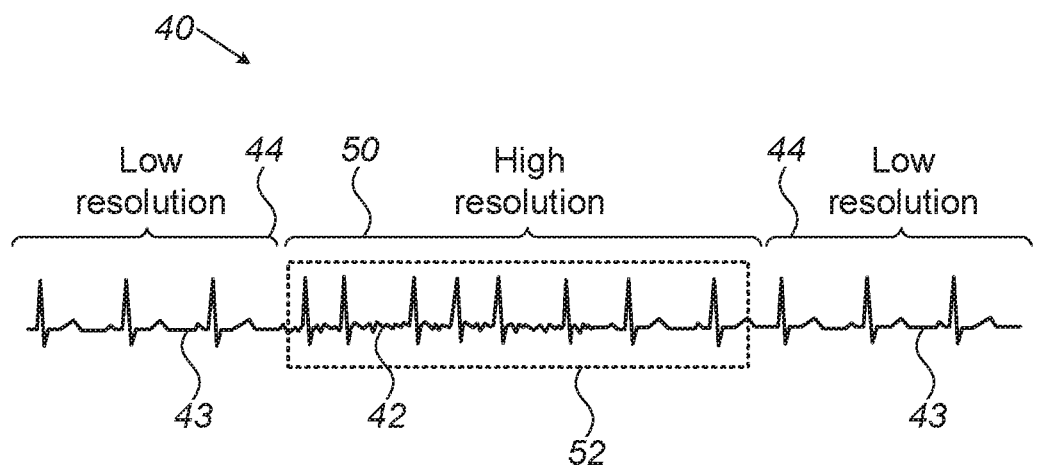
FIG. 2 is a pictorial illustration of a physician related electrocardiogram (ECG) time-intervals of data selected for compression, in accordance with an embodiment of the present invention.

FIG. 2 is a pictorial illustration of a physician related electrocardiogram (ECG) time-intervals of data selected for compression, in accordance with an embodiment of the present invention. Displayed ECG trace 40 shows normal cardiac rhythm 43 interrupted by a period of arterial fibrillation that is characterized, for example, by a small dense irregular wave pattern 42 between periods of normal heartbeats. In an embodiment, using an interactive means such as a touchscreen display or a mouse, physician 27 selects a time-interval 52 of to be uploaded in high resolution 50 to a remote server, while the rest of the displayed ECG trace 40 will be uploaded, for example, by a default low resolution 44, as further described below.

The example illustration shown in FIG. 2 is chosen purely for the sake of conceptual clarity. FIG. 2 shows only elements relevant to embodiments of the present invention. Other types of displayable medical data, such as electroanatomical maps, may be selectively compressed to be "smartly" uploaded to a cloud server. For example, physician 27 may select an area of a displayed electroanatomical map that contains information about a tissue site causing arrhythmia, to be compressed in a high resolution, while the rest of the map is compressed in low resolution. In another embodiment, processor 28 automatically identifies and selects data, such as in time-interval 52, and selectively compresses the selected data in high resolution.

Figure 3:
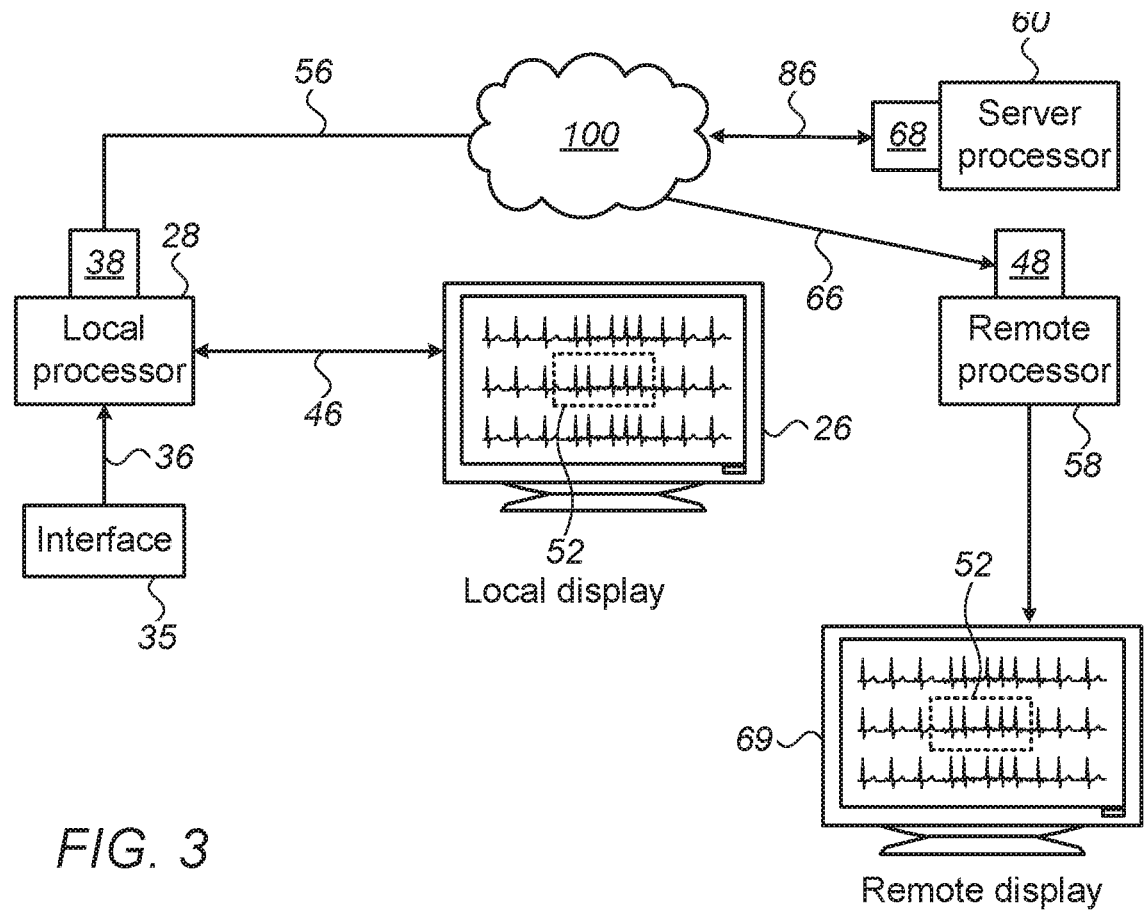
FIG. 3 is a block diagram that schematically illustrates a work flow during which ECG data is processed and communicated, in accordance with an embodiment of the present invention.

FIG. 3 is a block diagram that schematically illustrates a work flow during which ECG data is processed and communicated, in accordance with an embodiment of the present invention. The displayable data is selectively compressed by a local processor, uploaded by the local processor, which is connected with a NIC to the network, to a cloud server, downloaded to a remote processor that decompresses and displays the selectively compressed data.

FIG. 3 shows how acquired data, such as several hundred ECG channels of 32 bps, is transmitted to a local processor 28 via interface 35. In some embodiments, processor 28 calculates respective ECG traces and/or electrophysiological maps. Physician 27, inspecting the data on local display 26, for example, evaluates the calculated ECG traces to identify irregularities, selects time-intervals 52 of the ECG traces for processor 28 to compress in high resolution and transmit for additional diagnosis. Link 46 between processor 28 and display 26 is two-way, which enables physician 27 to transmit the selection. The resolution can be the original one or lower, for example, 32 bps or 16 bps. The remaining data is compressed by processor 28 in low resolution of, for example, 8 bps.

Processor 28, which is connected to a communication network 100 by a network interface, such as a Network-Interface-Card (NIC) 38, and a link 56, transmits (i.e., uploads) the selectively compressed ECG traces to a remote server 60. Compressed data may be uploaded, for example, with link 56 supporting an upload rate of 10 megabit/sec. In an embodiment, cloud server 60 is bidirectionally connected to network 100 via a NIC 68 and a link 86. Cloud server 60 receives the selectively compressed ECG traces and performs additional steps of data manipulation, saving, and archiving. In some embodiments, the selectively compressed ECG traces that were sent via network 100 to remote server 60 are downloaded by a remote user to a remote processor 58, which is connected to network 100 via a link 66 and a NIC 48, and are decompressed by remote processor 58 that furthermore presents the decompressed data on a remote display 69. A medical expert may view the ECG traces on remote display 69 and provide diagnosis from a distant location.

The example block diagram shown in FIG. 3 is chosen purely for the sake of conceptual clarity. Other network elements may exist, such as additional servers and switches. More than one remote location may be addressed for displaying downloaded data. Transfer of other types of displayable medical data may also benefit from selective compression, such as electroanatomical maps.

Figure 4:
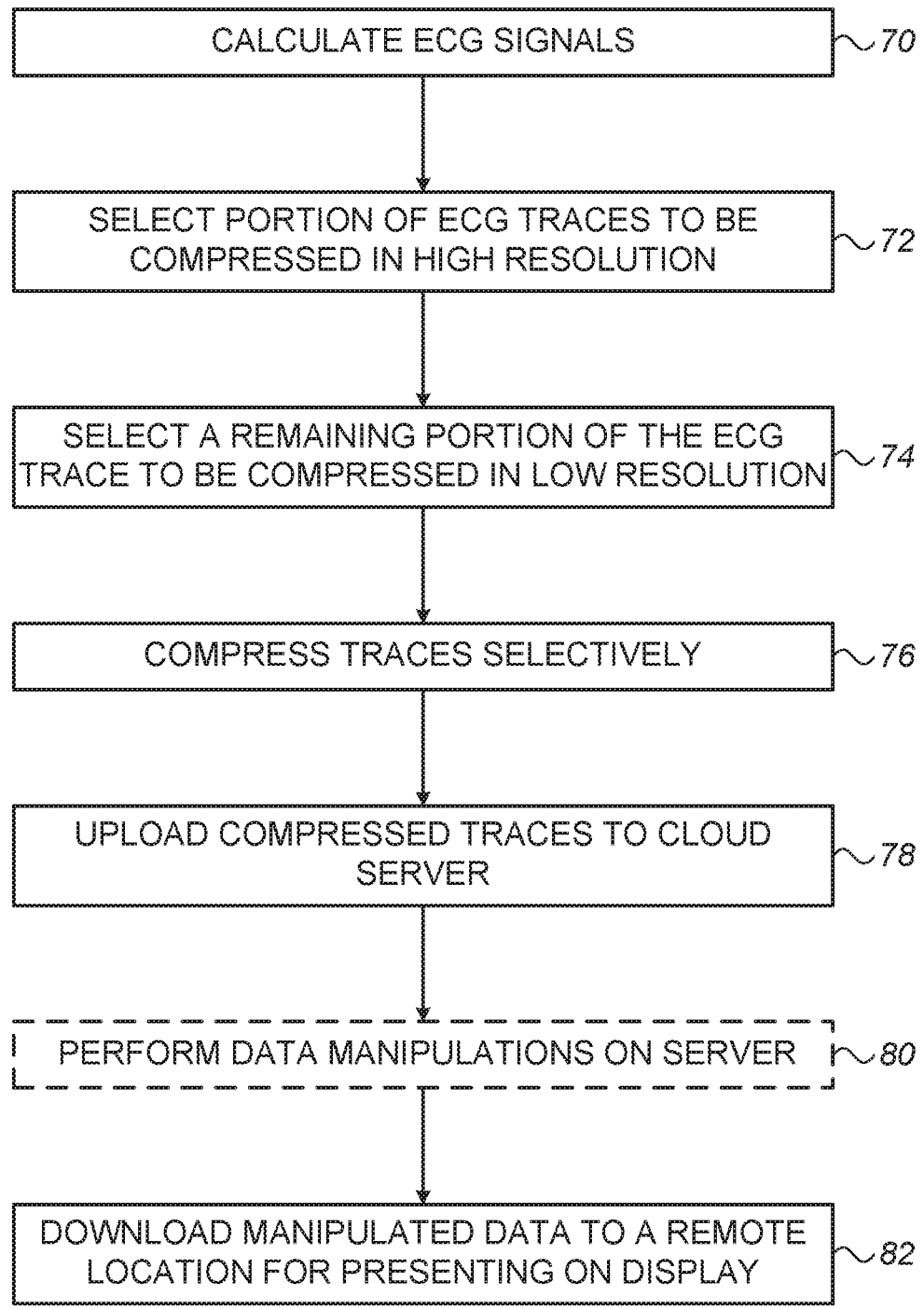
FIG. 4 is a flow chart that schematically illustrates a method for selectively compressing ECG data and remotely displaying the selectively compressed data, in accordance with an embodiment of the present invention.

FIG. 4 is a flow chart that schematically illustrates a method for selectively compressing ECG data and remotely displaying the selectively compressed data, in accordance with an embodiment of the present invention. The process begins with processor 28 calculating ECG traces to present to physician 27 on local display 26, at a local displaying step 70. Next, physician 27 inspects the ECG traces presented on display 26 and selects (e.g., on display 26, using interactive means such as a pointing and/or time-interval selection tool) time-intervals 52 (i.e., a portion) of the ECG traces to be compressed at high resolution by processor 28, at a selection of compression in high resolution step 72. Physician 27 selects another portion (e.g., a remaining portion) of the data to be compressed at low resolution by processor 28, at a selection of compression in low resolution step 74.

At selective compression step 76, processor 28 executes the selective compression, at high and low resolution, as selected at steps 72 and 74. Next, processor uploads the selectively compressed data to cloud processor 60, at an uploading step 78. In an optional data remote manipulation step 80, cloud processor 60 performs actions such as additional calculations and/or archiving. At a downloading step 82, either as predetermined or upon request, cloud server 60 downloads the selectively compressed data to a remote location for presentation on a display, for example, for evaluation by another physician.

The example flow chart shown in FIG. 4 is chosen purely for the sake of conceptual clarity. In alternative embodiments, for example, instead of selecting on display 26, the selection of a displayable data is performed by a processor employing a software, as described above.

Although the embodiments described herein mainly address selectively compressing electrophysiological data, the methods and systems described herein can also be used in other medical applications, such as in the processing of medical images. The methods and systems described herein can also be used in other fields, such as in gaming, virtual reality, and automotive appliances.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus for efficiently processing patient health data, comprising:
   a network interface, configured to communicate over a communication network; and
   a processor, configured to:
      receive (i) data, comprising a medical parameter acquired as a function of time, and (ii) a selection of one or more time intervals of interest within the time period;
      compress a first portion of the data, which is within the selected one or more time intervals, at a first high resolution;
      compress a second portion of the data, which is outside the selected one or more time intervals, at a second resolution, which is lower than the first high resolution; and
      transmit the compressed first and second portions of the data, via the network interface, over the communication network.

2. The apparatus according to claim 1, and comprising an input device, configured to receive the selection of the one or more time intervals from a physician.

3. The apparatus according to claim 1, wherein the processor is further configured to automatically select the one or more time intervals, based on a given criterion.

4. The apparatus according to claim 1, wherein the first resolution is at least twice the second resolution.

5. The apparatus according to claim 1, wherein the received data comprises one or more electrocardiogram (ECG) traces.

6. The apparatus according to claim 5, wherein the processor is configured to select the first resolution based on an average heart rate calculated over the selected time-intervals.

7. The apparatus according to claim 5, wherein the processor is configured to select the one or more time-intervals based on one or more indications that an arrhythmia was recorded during the time-intervals.

8. An apparatus for efficiently processing patient health data, comprising:
   a network interface, configured to communicate over a communication network; and
   a processor, configured to:
      receive over the communication network, via the network interface, data comprising a medical parameter acquired as a function of time, wherein the data comprises (i) a first portion that is within one or more selected time intervals and is compressed at a first high resolution, and (ii) a second portion that is outside the one or more selected time intervals and is compressed at a second resolution, lower than the first high resolution; and
      decompress the first and second portions of the data, and process the decompressed data.

9. The apparatus according to claim 8, wherein the processor is configured to archive the decompressed data.

10. The apparatus according to claim 8, wherein the processor is configured to transmit over the communication network, via the network interface, the decompressed first and second portions of the data to a remote processor.

11. A method for efficiently processing patient health data, comprising:
   in a processor, receiving (i) data, comprising a medical parameter acquired as a function of time, and (ii) a selection of one or more time intervals of interest within the time period;
   compressing a first portion of the data, which is within the selected one or more time intervals, at a first high resolution;
   compressing a second portion of the data, which is outside the selected one or more time intervals, at a second resolution, which is lower than the first high resolution; and
   transmitting the compressed first and second portions of the data over a communication network.

12. The method according to claim 11, wherein receiving the selection comprises receiving the selection of the one or more time intervals from a physician using an input device.

13. The method according to claim 11, and comprising automatically selecting the one or more time intervals, based on a given criterion.

14. The method according to claim 11, wherein the first resolution is at least twice the second resolution.

15. The method according to claim 11, wherein receiving the data comprises receiving one or more electrocardiograms (ECG) traces.

16. The method according to claim 15, and comprising selecting the first resolution based on an average heart rate calculated over the selected time-intervals.

17. The method according to claim 15, wherein selecting the one or more time-intervals comprises selecting the one or more time-intervals based on one or more indications that an arrhythmia was recorded during the time-intervals.

18. A method for efficiently processing patient health data, comprising:

in a processor, receiving over a communication network data comprising a medical parameter acquired as a function of time, wherein the data comprises (i) a first portion that is within one or more selected time intervals and is compressed at a first high resolution, and (ii) a second portion that is outside the selected one or more time intervals and is compressed at a second resolution, lower than the first high resolution; and decompressing the first and second portions of the data, and processing the decompressed data.

19. The method according to claim 18, and comprising archiving the decompressed data using the processor.

20. The method according to claim 18, and comprising transmitting the decompressed first and second portions of the data to a remote processor over the communication network.

* * * * *